(12) United States Patent
Feiweier

(10) Patent No.: US 8,436,613 B2
(45) Date of Patent: May 7, 2013

(54) METHOD AND MAGNETIC RESONANCE SYSTEM FOR DIFFUSION-WEIGHTED ACQUISITION OF MR SIGNALS

(75) Inventor: Thorsten Feiweier, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 559 days.

(21) Appl. No.: 12/773,121

(22) Filed: May 4, 2010

(65) Prior Publication Data

US 2010/0277169 A1    Nov. 4, 2010

(30) Foreign Application Priority Data

May 4, 2009   (DE) .......................... 10 2009 019 895

(51) Int. Cl.
 *G01V 3/00*   (2006.01)
(52) U.S. Cl.
 USPC ......................................... 324/309; 324/307
(58) Field of Classification Search .................. 324/309, 324/307, 306, 314, 312, 300
 See application file for complete search history.

(56) References Cited

U.S. PATENT DOCUMENTS

| | | | |
|---|---|---|---|
| 6,842,000 B2 | 1/2005 | Norris et al. | |
| 7,804,299 B2 * | 9/2010 | Reeder et al. ................. | 324/309 |
| 7,994,784 B2 * | 8/2011 | Yanasak et al. ............... | 324/307 |
| 8,125,223 B2 * | 2/2012 | K.N. et al. .................... | 324/309 |
| 8,134,363 B2 * | 3/2012 | Yanasak et al. ............... | 324/307 |
| 2007/0167732 A1 | 7/2007 | Zwanger | |
| 2008/0275329 A1 | 11/2008 | Reeder et al. | |
| 2010/0134104 A1 * | 6/2010 | Song et al. .................... | 324/309 |

OTHER PUBLICATIONS

"Eddy Current-Nulled Diffusion Weighting," Heid, Proc. Intl. Soc. Mag. Reson. Med., vol. 8 (2000) p. 799.
"Reduction of Eddy-Current-Induced Distortion in Diffusion MRI Using a Twice-Refocused Spin Echo," Reese et al., Magnetic Resonance in Medicine, vol. 49 (2003), pp. 177-182.
"Compensation of Maxwell Cross-Terms in Diffusion-Weighted Imaging," Zwanger et al., Proc. Intl. Soc. Mag. Reson. Med., vol. 11 (2004) p. 101.
"Concomitant Field Terms for Asymmetric Gradient Coils: Consequences for Diffusion, Flow and Echo-Planar Imaging," Meier et al., Magnetic Resonance in Medicine, vol. 60 (2008), pp. 128-134.
"Spin Diffusion Measurements: Spin Echoes in the Presence of a Time-Dependent Field Gradient," Stejskal et al., Journal of Chemical Physics. vol. 42, No. 1 (1965) pp. 288-292.
"Coherence-Induced Artifacts in Large-Flip-Angle Steady-State Spin-Echo Imaging,"Vasilic et al., Magnetic Resonance in Medicine, vol. 52 (2004), pp. 346-353.
"Categories of Coherence Pathways for the CPMG Sequence," Song, Journal of Magnetic Resonance, vol. 157 (2002) pp. 82-91.

* cited by examiner

Primary Examiner — Louis Arana
(74) Attorney, Agent, or Firm — Schiff Hardin LLP

(57) ABSTRACT

In a method for diffusion-weighted acquisition of MR signals with an acquisition sequence that includes a diffusion module with multiple diffusion coding gradients and a readout module with readout gradients to acquire the MR signals, the acquisition sequence is configured to acquire MR signals that correspond to a predetermined signal coherence path. The method includes the acquisition of MR signals with the acquisition sequence, and the diffusion coding gradients are activated with predetermined gradient moments during the acquisition sequence. The gradient moments of the diffusion coding gradients are set such that MR signals that correspond to other coherence paths than the predetermined coherence path are reduced, wherein the adjustment of the gradient moments to achieve a predetermined reduction ensues on the basis of a threshold.

22 Claims, 5 Drawing Sheets

METHOD AND MAGNETIC RESONANCE SYSTEM FOR DIFFUSION-WEIGHTED ACQUISITION OF MR SIGNALS

BACKGROUND OF THE INVENTION

1. Field of the Invention

The present invention concerns a method for diffusion-weighted acquisition of MR signals with an acquisition sequence that includes multiple diffusion coding gradients, and a magnetic resonance system for implementing such a method.

2. Description of the Prior Art

Diffusion-weighted magnetic resonance (MR) images in the clinical routine can deliver important diagnostic information, for example in stroke and tumor diagnostics. In diffusion-weighted imaging (DWI), diffusion coding gradients with high amplitude and long pulse duration are used in combination with a suitable readout or image data acquisition module. The sensitivity to the diffusion follows from the fact that the diffusion of water molecules reduces along the applied field gradients of the magnetic resonance (MR) signal. In regions of an examined subject with low diffusion, a lower signal loss thus occurs, and the regions are accordingly imaged with a higher signal intensity. The strength of the diffusion weighting is correlated with the strength of the diffusion coding gradients. The diffusion weighting is characterized by what is known as the b-value, which is a function of gradient parameters (for example the gradient strength, duration or the interval between gradients). To avoid movement artifacts, a "single shot" readout module can be used, for example, with which a complete raw data set is acquired during a single acquisition sequence. For example, an echoplanar imaging sequence (EPI) can be used.

The most prevalent method for diffusion coding uses the monopolar spin echo acquisition sequence described by Stejskal and Tanner (see "Spin Diffusion Measurements Spin Echoes in the Presence of a Time-Dependent Field Gradient" in The Journal of Chemical Physics 42, 1965). In this method, two strongly symmetrical gradients are positioned on each side of a 180° refocusing pulse in a spin echo sequence. These symmetrical diffusion coding gradients have the purpose of accelerating the signal loss caused by the diffusion by promoting the dephasing. The dephasing is normally proportional to the square of the time during which the gradient is switched (activated) (gradient pulse length), to the time interval of the two gradient pulses and to the square of the strength of the switched gradient field.

The signal-to-noise ratio (SNR) and geometric distortions are crucial to the quality of acquired images. Furthermore, the gradient systems that are used limit the maximum switchable strength of the magnetic field gradients. The imaging parameter that is relevant to the signal-to-noise ratio is the echo time TE. The geometric distortions are based on spatial variations of the basic field amplitude $B_0$, wherein EPI is especially sensitive to this. Static distortions are caused by the basic field inhomogeneity and the susceptibility of different regions of the examination subject. Dynamic distortions (for example eddy current effects) are in particular affected by the temporal sequence of the gradient pulses. Every activation and deactivation of field gradients can cause such eddy currents that decay with different time constants. With a slow decay, field components can remain until the readout, such that disruptions and distortions of the acquired MR data can result. Particularly in the combination of images acquired with different diffusion gradient directions and amplitudes, it is desirable to keep the dynamic distortions as small as possible in order to reduce errors in the resulting data (for example anisotropy maps, diffusion maps, tensor data and the like).

The monopolar spin echo acquisition sequence described by Stejskal and Tanner exhibits strong geometric distortions, in particular a high proportion of residual eddy current fields, and a high loading of the gradient system. To avoid the strong distortions, further-developed acquisition sequences use bipolar double spin echo schemes that can implicitly compensate the eddy current fields. Such a scheme is described by, for example, T. G. Reese et al.: Magnetic Resonance in Medicine 49:177 (2003). Disadvantages of the monopolar scheme can be reduced with such a scheme, but at the cost of a longer echo time. For example, the additional radio-frequency (RF) pulse that is to be used requires 5 ms. Due to relaxation time properties of the examined tissue, the longer echo time can disadvantageously affect the image quality. Furthermore, additional unwanted signal coherence paths are introduced by the additional RF pulses, which can lead to additional unwanted spin echo signals or stimulated echo signals as well as to free induction decay signals. These additional coherence paths cause artifacts in the image data that are reconstructed from the acquired MR data. Spoiler gradients are known for suppression of such unwanted coherence paths. However, such additional gradients in turn extend the echo time (TW) and thus disadvantageously affect the signal-to-noise ratio. A more complicated echo is also necessary with these.

It is desirable to efficiently suppress the image artifacts caused by the additional signal coherence paths. The echo time should not be extended by this in order to achieve a good signal-to-noise ratio. It is also desirable to keep the distortions low given an optimal utilization of the gradient system.

SUMMARY OF THE INVENTION

An object of the present invention is to provide an improved method for diffusion-weighted acquisition of MR signals as well as a magnetic resonance system with which an improved diffusion-weighted acquisition can be implemented.

According to a first aspect of the present invention, a method for diffusion-weighted acquisition of MR signals with an acquisition sequence is provided that includes a diffusion module with multiple diffusion coding gradients and a readout module with readout gradients to acquire the MR signals. The acquisition sequence is configured to acquire MR signals that correspond to a predetermined signal coherence path. The method includes the acquisition of MR signals with the acquisition sequence, wherein the diffusion coding gradients are activated with predetermined gradient moments during the acquisition sequence. The gradient moments of the diffusion coding gradients are set such that MR signals that correspond to other coherence paths than the predetermined coherence path are reduced. The adjustment of the gradient moments to achieve a predetermined reduction ensues on the basis of a threshold.

The diffusion module can also be designated as a diffusion sequence, and can include, for example, RF pulses for excitation or for rephasing in addition to multiple diffusion coding gradients. The desired diffusion weighting and direction can be set by means of the gradient moments of the diffusion coding gradients. The readout module can include, for example, readout gradients in the form of phase coding gradients or frequency coding gradients. Coherence paths can define the creation of different signals due to RF pulses that, for example, are radiated during the acquisition sequence. Every RF pulse can generate a free induction decay signal that can in turn generate echo signals or stimulated echo signals (that can be described with such coherence paths) given the presence of additional rephasing gradients.

Artifacts in the image data reconstructed from the MR signals can be avoided by the adjustment of the diffusion coding gradients to suppress the unwanted coherence paths. Since the suppression of these unwanted signal portions is not achieved by additional gradients but rather by adjusting the diffusion coding gradients, the duration of the acquisition sequence is not extended, such that an improved signal-to-noise ratio can be achieved with the method. Moreover, by using a threshold it can be ensured that a predetermined reduction of the unwanted coherence paths is achieved.

In one embodiment of the present invention, the threshold can be determined depending on the readout module that is used. An effective suppression of the unwanted signal portions can therefore also be achieved given readout modules that use a "single shot" scheme.

For example, the threshold can be determined on the basis of a resulting gradient moment ($M_{readout}$) of the readout gradient of the readout module. Given use of stronger readout gradients, for example, the threshold is also increased so that an effective suppression of the unwanted coherence paths can be ensured.

The threshold can define a minimum dephasing gradient moment, wherein the adjustment of the gradient moments of the diffusion coding gradients ensues such that the gradient moment resulting from the diffusion coding gradients is at least as large as the minimum dephasing gradient moment. The adjustment of the gradient moments of the diffusion coding gradients can ensue, for example, such that, for each of the other coherence paths of the acquisition sequence (i.e. the unwanted coherence paths), the gradient moment that results for the respective coherence path from the diffusion coding gradient is at least as large as the minimum dephasing gradient moment. Different diffusion coding gradients can be effective for different coherence paths, such that a separate consideration of the coherence paths and a corresponding adjustment of the diffusion coding gradients is advantageous.

The threshold can be determined such that the central k-space positions of the MR signals that correspond to the other coherence paths of the acquisition sequence lie outside of k-space that is to be scanned with the acquisition sequence. By the adjustment of the diffusion coding gradients on the basis of the threshold, the central k-space positions of the unwanted MR signals can thus be shifted to positions outside of the region of k-space for which MR signals are acquired with the acquisition sequence.

The threshold can be a minimal dephasing gradient moment $M_{spoil}$ and be determined according to the equation $M_{spoil}=N \cdot M_{readout}$, wherein $N \geq 1$. The readout gradient $M_{readout}$ can thereby be determined according to $M_{readout}=RES/(\gamma FOV)$, wherein RES designates the resolution, FOV designates the field of view of the readout module and $\gamma$ designates the gyromagnetic ratio.

The gradient moments of the diffusion coding gradients can be adjusted by means of the gradient pulse lengths, for example. The diffusion module can comprise at least four diffusion coding gradients with at least four gradient pulse lengths as parameters. Three of the parameters can be determined by three conditions established by the acquisition sequence, and the at least one remaining parameter can be determined on the basis of the threshold. For example, the at least one remaining parameter can be determined from a comparison of the gradient moments of the diffusion coding gradients that result for the other coherence paths with the threshold. For example, the following conditions can be taken into account for the adjustment of the gradient pulse lengths: a total duration of the switching of the diffusion coding gradients that is provided by the acquisition sequence; a rephasing of the magnetization that corresponds to the predetermined coherence paths that is to be achieved by the diffusion coding gradients; and an adaptation of the gradient pulse durations such that a rephasing of a spin echo that is to be generated by the acquisition sequence occurs at a predetermined acquisition point in time of the readout module. The last condition can correspond, for example, to a condition for the echo time given a double spin echo (DSE) sequence, wherein the time between the rephasing pulses of the DSE sequence should correspond to the sum of the time between excitation pulse and first rephasing pulse and second rephasing pulse and acquisition point in time.

In one embodiment, the diffusion module includes at least four diffusion gradients, wherein two gradients are respectively activated in opposite directions. Two gradients switched in opposite directions can also be designated as a bipolar gradient. Eddy currents can be effectively suppressed with such gradients and the gradient system of the MR system can be optimally utilized.

The readout module can be an echoplanar imaging (EPI) readout sequence or a segmented echoplanar imaging (EPI) readout sequence.

In a further embodiment, the diffusion module furthermore includes multiple dephasing gradients that produce a reduction of the MR signals that correspond to the other coherence paths. The additional dephasing gradients can thus support the suppression of the unwanted signal coherence paths. The dephasing gradients can be provided as a pair of identical gradients, wherein one gradient of the pair can occur before a refocusing pulse of the diffusion module and the other can occur after.

The gradient moments of the dephasing gradients and/or the polarity of the dephasing gradients can be adjusted depending on the threshold. If the threshold is dependent on the readout module, it can thereby be ensured that unwanted signal paths are efficiently suppressed even given small b-values.

The dephasing gradients can be superimposed on the diffusion gradients. For example, an extension of the TE time thus can be avoided even given the use of the additional dephasing gradients, so an improved signal-to-noise ratio is achieved.

The dephasing gradients are then advantageously switched when the amplitude ($G_D$) of the diffusion coding gradients falls below a predetermined amplitude threshold. For example, diffusion coding gradients with low amplitudes are used for diffusion imaging with small b-values so that a suppression of the unwanted coherence paths possibly occurs only insufficiently. The amplitude threshold can now be established such that the additional dephasing gradients are switched given an inadequate suppression by the diffusion coding gradients, such that an effective suppression is achieved even for small b-values.

The gradient moments of the dephasing gradients can thereby be adjusted depending on the amplitude of the diffusion coding gradients.

For example, the threshold can define a minimal dephasing gradient moment, wherein the adjustment of the gradient moments of the diffusion coding gradients and the dephasing gradients can ensue such that, for each of the other coherence paths of the acquisition sequence, the gradient moment which results for the respective coherence path from the diffusion coding gradients and the dephasing gradients is at least as large as the minimal dephasing gradient moment ($M_{spoil}$). For the individual coherence paths, conditions can thus be set in turn on the basis of which both the parameters of the diffusion coding gradients and those of the dephasing gradients can be adjusted.

Furthermore, the diffusion module can include a pause with variable duration between at least two diffusion coding gradients in order to provide an additional degree of freedom for the selection of the gradient moments of the diffusion coding gradients.

The acquisition sequence can comprise a double spin echo sequence with two refocusing pulses. For example, at least three free induction decays, three spin echoes and two stimulated echoes can then occur as other coherence paths. The adjustment of the gradient moments of the diffusion coding gradients can then ensue so that the MR signal portions that correspond to these coherence paths are reduced.

The methods described above can be implemented automatically, for example by a control unit or a computer of a magnetic resonance system.

According to a further aspect of the present invention, a magnetic resonance system is provided for diffusion-weighted acquisition of MR signals with an acquisition sequence that comprises a diffusion module with multiple diffusion coding gradients and a readout module with readout gradients to acquire the MR signals, wherein the acquisition sequence is configured to acquire MR signals that correspond to a predetermined signal coherence path. The magnetic resonance system includes: an acquisition unit that is designed to acquire MR signals with the acquisition sequence and to switch the diffusion coding gradients with predetermined gradient moments during the acquisition sequence; and a control unit that is designed to control the acquisition unit. The control unit adjusts the gradient moments of the diffusion coding gradients such that MR signals that correspond to other coherence paths than the predetermined coherence path are reduced, wherein the adjustment of the gradient moments to achieve a predetermined reduction ensues on the basis of a threshold. Advantages similar to those mentioned above can be achieved with such a magnetic resonance system.

According to a further aspect of the present invention, a computer-readable storage medium encoded with a computer program is provided. The computer program executes any of the aforementioned method embodiments upon execution in a computer system that, for example, is functionally connected with a magnetic resonance system. Such a computer program can be executed on a computer or control unit of a magnetic resonance system, for example.

DESCRIPTION OF THE PREFERRED EMBODIMENTS

Figure 1:
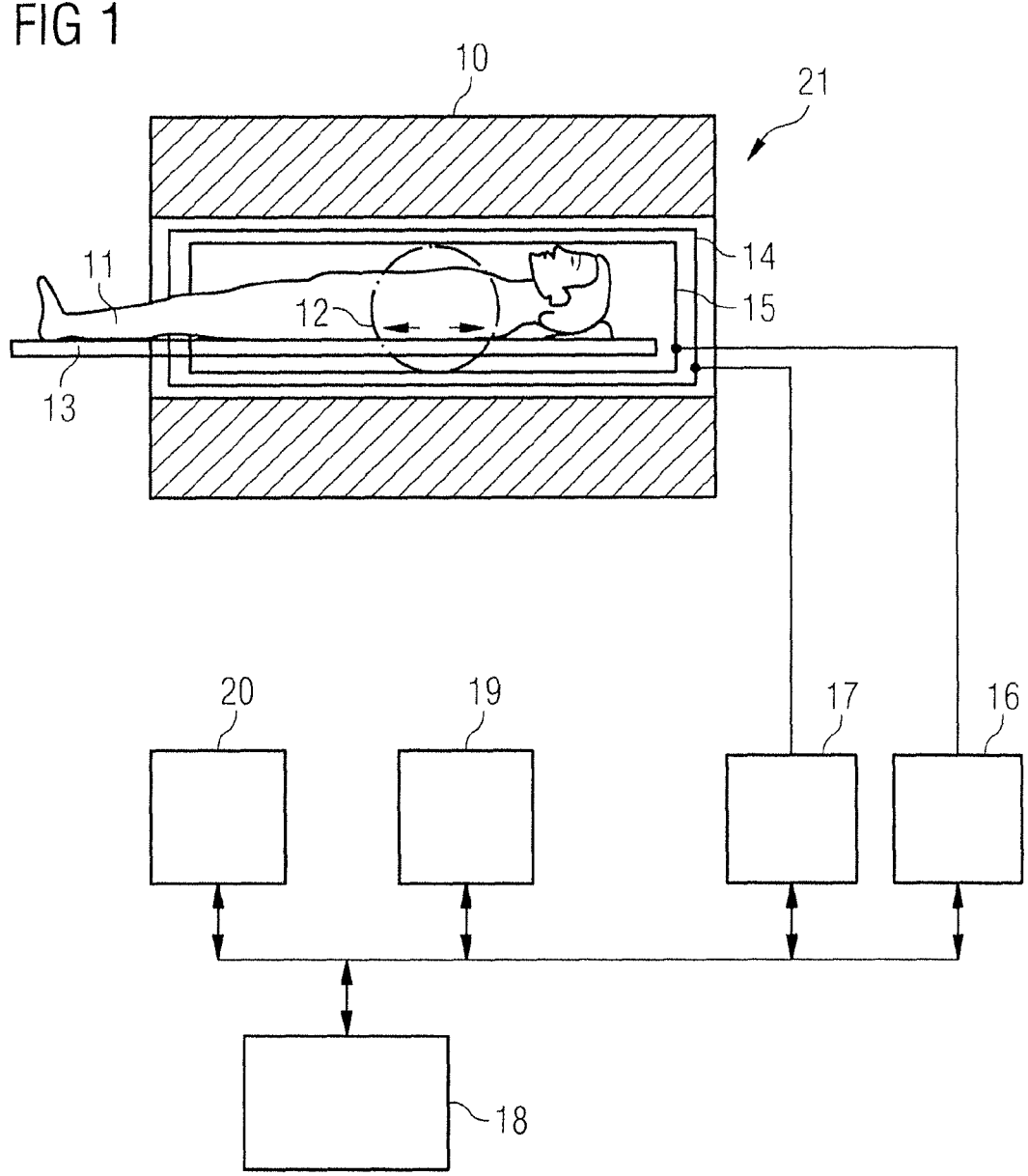
FIG. 1 schematically illustrates an embodiment of a magnetic resonance system according to the invention.

FIG. 1 schematically shows a magnetic resonance system that is configured to acquire magnetic resonance data to implement diffusion-weighted imaging. Such a magnetic resonance system has a magnet 10 to generate a polarization field $B_0$. An examination subject (here an examination person 11) can be slid into the magnet 10 on a recumbent table 13 (as is schematically depicted by the arrows). The MR system furthermore has a gradient system 14 to generate magnetic field gradients that are used for the imaging and spatial coding. Furthermore, diffusion coding gradients can be generated with the gradient system 14 for diffusion-weighted imaging.

For excitation of the polarization resulting in the basic magnetic field, a radio-frequency coil arrangement 15 is provided that radiates a radio-frequency (RF) field into the examined person 11 in order to deflect the magnetization out of the steady (equilibrium) state. For example, both excitation pulses (for instance 90° sinc pulses) or rephasing pulses (for example 180° pulses) can be radiated by means of the RF coil arrangement 15. To control the magnetic field gradients, a gradient unit 17 is provided, and an RF unit 16 is provided to control the radiated RF pulses. Gradient system 14 and radio-frequency coil arrangement 15 as well as RF unit 16 and gradient unit 17 can be designated together as an acquisition unit 21.

The magnetic resonance system is centrally controlled by the control unit 18, which also can comprise a computer (for example to reconstruct image data). Control unit 18 controls the radiation of RF pulses, the application of gradients and the acquisition of resulting MR signals. An operator can select a sequence protocol via an input unit 19 and can input and modify imaging parameters that are displayed via a display 20. For example, a b-value can be selected with which a diffusion-weighted imaging sequence should be implemented.

The magnetic resonance system schematically shown in FIG. 1 can naturally include additional components that magnetic resonance system conventionally possess. The general mode of operation of an MR system is known to those skilled in the art, such that a detailed description of the general components need not be provided herein.

Figure 2:
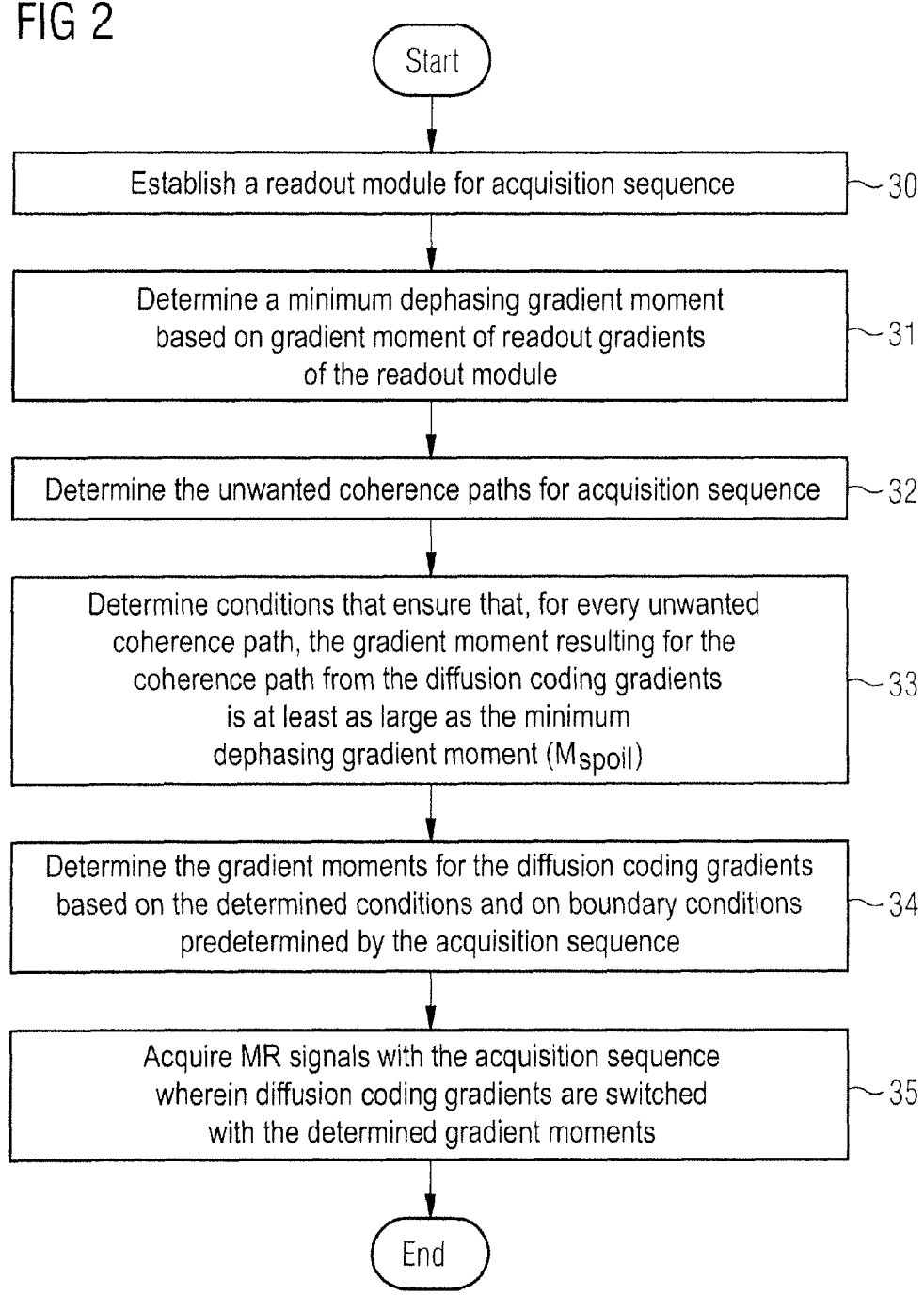
FIG. 2 is a flow diagram of an embodiment of the method according to the invention.
Figure 3:
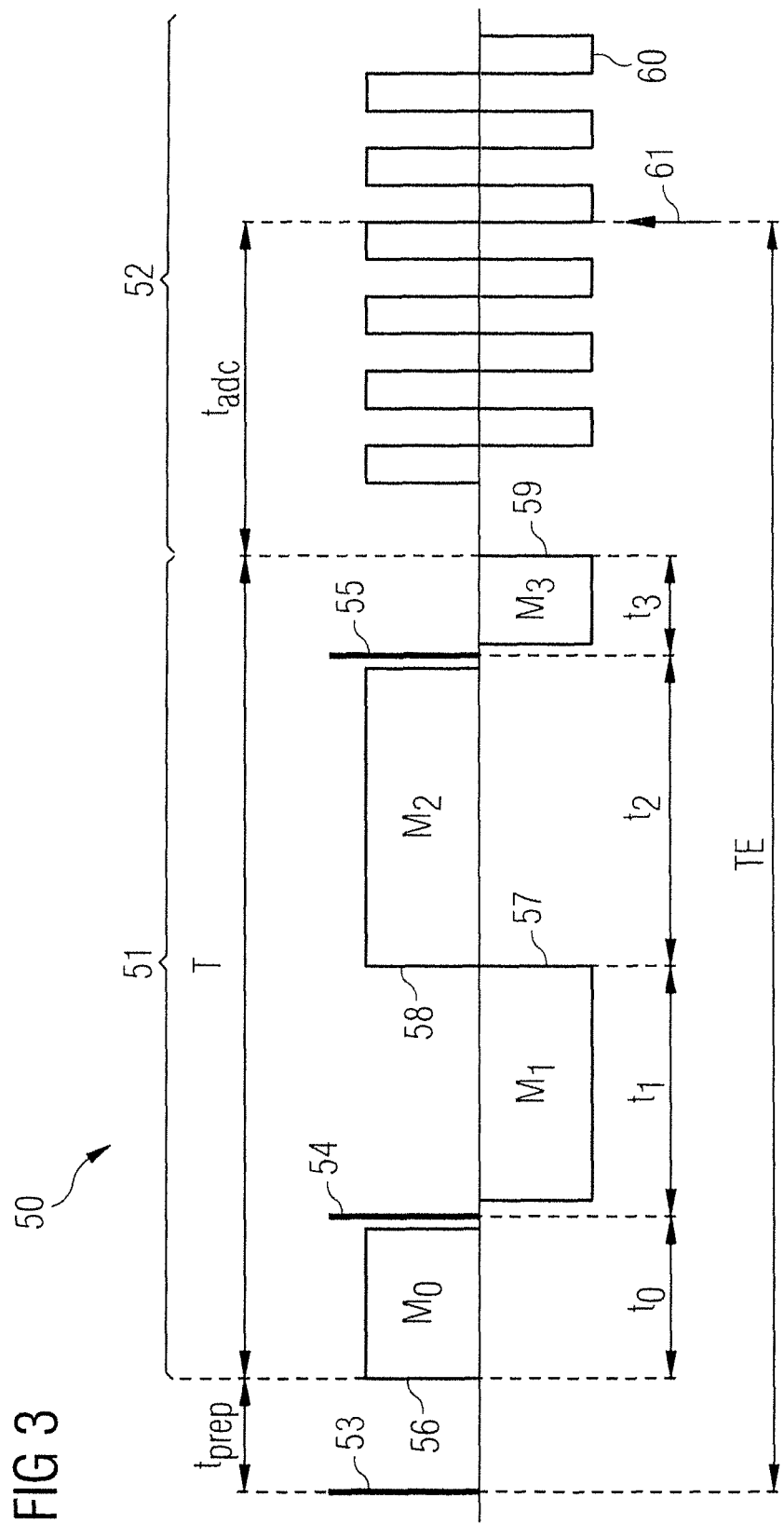
FIG. 3 shows a time progression diagram of an embodiment of the method according to the invention.
Figure 4:
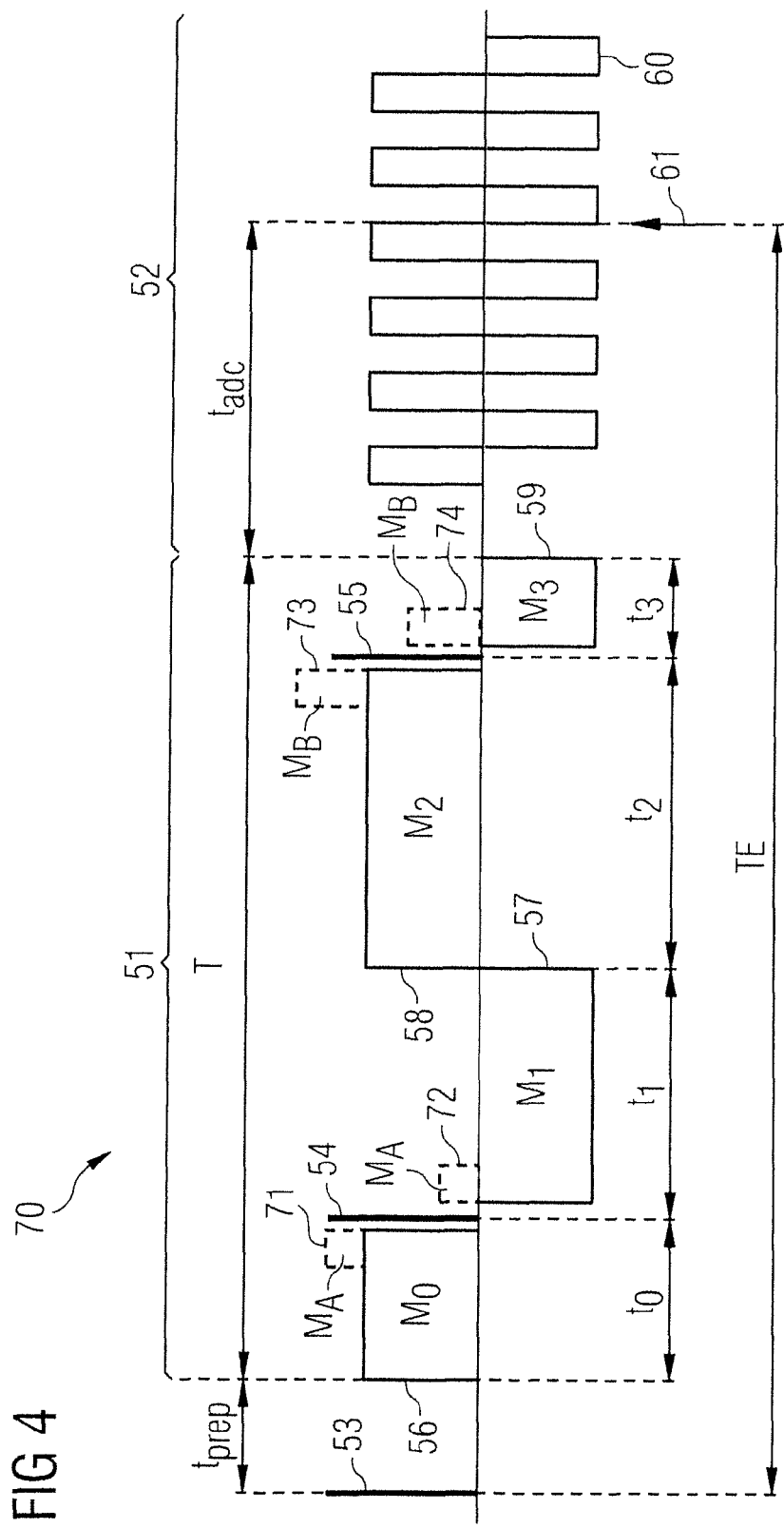
FIG. 4 shows a time progression diagram of an additional embodiment of the method according to the invention.

Control unit 18 is now designed such that it implements an acquisition sequence by means of the acquisition unit 21, as the acquisition sequence is shown in FIG. 3 or FIG. 4 The acquisition sequence can comprise different readout modules, for example an echoplanar imaging readout sequence. Upon switching the diffusion coding gradients, the control unit 18 can vary the amplitude and/or gradient pulse length in order to adjust a specific gradient moment. In one embodiment, the control unit 18 adjusts the gradient moment of the diffusion coding gradients such that MR signals that result from unwanted coherence paths are suppressed. How such an adjustment can ensue is described in more detail in the following with reference to FIG. 2-6. for example, a double spin echo acquisition sequence can be used, wherein then only the MR signal which corresponds to the double spin echo coherence path should be registered. Other coherence paths, for example signals from free induction decay (FID) of the 180° pulses and individual spin echoes (SE) or stimulated spin echoes (STE), should be suppressed.

Control unit 18 can furthermore switch additional dephasing gradients or, respectively, spoiler gradients that can in particular be superimposed on the diffusion coding gradients.

Unwanted coherence paths can therefore be effectively suppressed even given low b-values.

FIG. 2 illustrates an embodiment of the method according to the invention that can be executed at the magnetic resonance system shown in FIG. 1, for example. In a first Step 30, an establishment of a readout module for the acquisition sequence that is to be used ensues. Various acquisition sequences to generate diffusion contrast are known to those skilled in the art, and these can be used with the method according to the present embodiment. Here a double spin echo sequence with bipolar diffusion coding gradients is used, for example. Such an acquisition sequence is illustrated in FIG. 3, for example. FIG. 3 shows the time progression of the acquisition sequence on one time axis; however, it should be clear that the gradients (only schematically shown) can be switched in different spatial directions, for example. The acquisition sequence 50 comprises an excitation pulse 53 and two rephasing pulses or refocusing pulses 54 and 55 to generate a double spin echo with the echo time TE, wherein the echo occurs in the k-space center 61. The diffusion module 51 of the acquisition sequence 50 comprises multiple diffusion coding gradients 56-59 with the gradient pulse lengths $t_i$ (i=0-3) and the gradient moments $M_i=G_D \cdot t_i$, wherein $G_D$ designates the amplitude of the gradients 56-59. A diffusion coding within the time span T ensues by means of these gradients. As can be seen, bipolar gradient pulses are used, meaning that two gradients are respectively switched in opposite directions.

The acquisition sequence 50 furthermore comprises a readout module 52 to sample k-space with a suitable trajectory. This ensues in turn by activation of different gradients (for example phase and frequency coding gradients), which is schematically illustrated by the gradients 60. For example, a meandering, echoplanar readout can ensue. A readout sequence of the echoplanar imaging (EPI) or a segmented echoplanar imaging can be used for this, for example.

Additional time intervals $t_{prep}$ and $t_{adc}$ are required before and after the diffusion coding, for example for navigator echoes, slice refocusing and acquisition of MR data for the first part of k-space. The diffusion coding strength of the shown acquisition sequence 50 can be described by a b-value that is proportional to the square of the amplitude of the coding gradients. Assuming negligible RF pulse durations, the b-value can be estimated as $$b = 2/3 \gamma^2 G_D^2 (t_0+t_1)^3. \quad (1)$$

Such a bipolar acquisition scheme has the advantage that the gradient load is distributed between positive and negative polarities, so the hardware of the gradient system can be optimally utilized, and that eddy currents are generally reduced.

Referring again to FIG. 2, the determination of a minimum rephasing gradient moment ($M_{spoil}$) ensues in a next Step 31 based on the gradient moment of readout gradients of the readout module. The minimum dephasing gradient moment (also called the spoiling moment $M_{spoil}$) represents a threshold, wherein an effective suppression of unwanted signal coherence paths can ensue with gradients above this threshold. This threshold is established depending on the readout module that is used. For example, a spoiling moment of at least N times the readout moment $M_{readout}$ is required for an EPI module. The threshold us used to establish the gradient moment of the diffusion coding gradients. The gradients are adjusted so that unwanted echoes occur outside of the scanned k-space region, for example. N=1 thereby designates the boundary (limit) of k-space, and given greater values of N the unwanted echo is shifted outward beyond the boundary of the region to be scanned. The threshold results at $M_{spoil}=N \cdot RES/(\gamma FOV)$ for an EPI readout module, wherein RES designates the number of pixels and FOV designates the field of view.

A determination of the unwanted coherence paths for the acquisition sequence ensues in Step 32. This is in turn illustrated in the acquisition sequence 50 of FIG. 3, for example. New coherence paths are generated with the acquisition sequence 50 shown in FIG. 3, for example. These are three free induction decays (FID) of the RF pulses 53-55, three spin echoes (SE), a stimulated echo (STE), an antistimulated echo (ASTE) and a double spin echo (DSE). The predetermined signal coherence path according to which MR signals should be acquired with the acquisition sequence 50 is the double spin echo (DSE). All other coherence paths can generate unwanted artifacts in reconstructed image data. According to the present embodiment, these other coherence paths should be suppressed via suitable adjustment of the moments of the diffusion coding gradients. For this purpose, a gradient moment that is at least as large as the predetermined threshold (i.e. the spoiling moment $M_{spoil}$) should act on these signal paths.

For this in Step 33 conditions are determined that ensure that, for each unwanted coherence path, the gradient moment resulting for the diffusion coding gradients for the coherence path is at least as large as the minimal dephasing gradient moment $M_{spoil}$. The following equations can be assembled for the example illustrated in FIG. 3:

$$\text{1. FID } |M_0-M_1+M_2-M_3| \geq M_{spoil} \quad (5a)$$

$$\text{2. FID } |-M_1+M_2-M_3| \geq M_{spoil} \quad (5b)$$

$$\text{3. FID } |-M_3| \geq M_{spoil} \quad (5c)$$

$$\text{1. SE } |M_0+M_1-M_2+M_3| \geq M_{spoil} \quad (5d)$$

$$\text{2. SE } |M_0-M_1+M_2+M_3| \geq M_{spoil} \quad (5e)$$

$$\text{3. SE } |-M_1+M_2+M_3| \geq M_{spoil} \quad (5f)$$

$$\text{STE } |M_0+M_3| \geq M_{spoil} \quad (5g)$$

$$\text{ASTE } |M_0-M_3| \geq M_{spoil} \quad (5h)$$

$$\text{DSE } M_0+M_1-M_2-M_3=0 \quad (5i)$$

In the equations, $M_0$-$M_3$ designate the gradient moments of the diffusion coding gradients 56-59. In the following it is assumed that all moments $M_0$-$M_3$ are positive, wherein the following calculation can also be implemented given a reversal of the algebraic sign. Using Equation (5i), $M_0$ can be defined as $M_0=-M_1+M_2+M_3$, and the equations can be simplified as $$\text{1. FID } 2|M_1-M_2| \geq M_{spoil} \quad (6a)$$

$$\text{2. FID } |-M_1+M_2-M_3| \geq M_{spoil} \quad (6b)$$

$$\text{3. FID } |M_3| \geq M_{spoil} \quad (6c)$$

$$\text{1. SE } 2|M_3| \geq M_{spoil} \quad (6d)$$

$$\text{2. SE } 2|M_1-M_2-M_3| \geq M_{spoil} \quad (6e)$$

$$\text{3. SE } |M_1-M_2-M_3| \geq M_{spoil} \quad (6f)$$

$$\text{STE } |M_1-M_2-2M_3| \geq M_{spoil} \quad (6g)$$

$$\text{ASTE } |M_1-M_2| \geq M_{spoil} \quad (6h)$$

Since $2|x| \geq |x|$ always applies, it is sufficient to take into account the following inequalities:

$$|M_1-M_2| \geq M_{spoil} \quad (7a)$$

$$|M_1-M_2+M_3| \geq M_{spoil} \quad (7b)$$

$$|M_3| \geq M_{spoil} \quad (7c)$$

$$|M_1-M_2-M_3| \geq M_{spoil} \quad (7d)$$

$$|M_1-M_2-2M_3| \geq M_{spoil} \quad (7e)$$

These can generally be satisfied in that $$M_3 \geq M_{spoil}+|M_1-M_2| \quad (8a)$$

$$|M_1-M_2| \geq M_{spoil} \quad (8b)$$

are set. By using the specific solution $$M_3 \geq 2|M_1-M_2| \quad (9a)$$

$$|M_1-M_2| \geq M_{spoil} \quad (9b)$$

the following calculations can be satisfied. However, it should be heeded that this specific solution places greater demands and the required gradient moment $M_3$.

Two different cases can that are designated in the following with "+" and "−" can now be differentiated. The first case is $M_1-M_2 \geq 0$ ("+") and the second case is $M_1-M_2 < 0$ ("−"). Since the gradient moments $M_i$ are provided by $G_D \cdot t_i$, the conditions (9) can simply be translated into time inequalities:

"+"                 "−"

$$t_3 \geq 2(t_1-t_2) \quad\quad t_3 \geq 2(t_2-t_1) \quad (10a)$$

$$t_1-t_2 \geq M_{spoil}/G_D \quad\quad t_2-t_1 \geq M_{spoil}/G_D \quad (10b)$$

The second condition is thereby dependent on the respective diffusion gradient amplitude $G_D$. The higher this amplitude, the simpler it is to satisfy these inequalities. With predetermined time durations it can possibly be difficult to find a valid result for every $G_D$ value. This should particularly be taken into account given the use of smaller b-values. This is subsequently discussed in detail with reference to FIG. 4. By using the maximum allowed value for $t_1-t_2$, the second condition can be relaxed:

"+"                 "−"

$$t_3 = 2(t_1-t_2) \quad\quad t_3 = 2(t_2-t_1) \quad (11a)$$

$$t_1-t_2 \geq M_{spoil}/G_D \quad\quad t_2-t_1 \geq M_{spoil}/G_D \quad (11b)$$

It is also possible to use the remaining degree of freedom in the selection of time $t_2$ to reduce remaining eddy currents.

Based on the conditions just described and on boundary conditions provided by the acquisition sequence, a determination of the gradient moments for the diffusion coding gradients ensues in Step 34 of FIG. 2. Given use of constant gradient amplitudes, this corresponds to a determination of the gradient pulse durations $t_1$.

For the double spin echo sequence illustrated in FIG. 3, the following boundary conditions can be set:

$$t_0+t_1=t_2+t_3 \quad (2)$$

$$t_{prep}+t_0+t_3+t_{adc}=t_1+t_2 \quad (3)$$

$$\Leftrightarrow TE-T+t_0+t_3=t_1+t$$

Equation (2) thereby ensures that a complete rephasing of the gradient moment occurs. Equation (3) is a condition that is defined by the point in time of the occurrence of the spin echo. The sum of the time spans between pulses 53 and 54 and pulse 55 and the occurrence of the spin echo 61 should be just as large as the time spans between the refocusing pulses 54 and 55. Furthermore, the total duration T for the radiation of the diffusion coding gradients can be defined as $$T=t_0+t_1+t_2+t_3 \quad (4)$$

These equations assume identical gradient amplitudes $G_D$ of the gradients and negligible gradient flanks and RF pulse durations. The echo time TE and the time spans T are provided by the imaging protocol, in particular by the desired diffusion sensitivity b. With three equations and four parameters, one degree of freedom consequently remains that, in the embodiment according to the invention, is chosen so that the unwanted coherence paths are suppressed. By suitable selection of this degree of freedom, the suppression can implicitly ensue via the diffusion coding gradients without additional spoiler gradients. The free parameter is established by the conditions determined in advance for the suppression of the unwanted coherence paths.

For this Equations (2)-(4) are initially modified as follows:

$$(4): t_0=T-t_1-t_2-t_3 \quad (12a)$$

$$(2): t_0+t_1=t_2+t_3$$

$$\Leftrightarrow T-t_1-t_2-t_3+t_3=t_2+t_3$$

$$\Leftrightarrow T=2(t_2+t_3)$$

$$\Leftrightarrow t_2=T/2-t_3 \quad (12b)$$

$$(3): TE-T+t_0+t_3=t_1+t_2$$

$$\Leftrightarrow TE-T+T-t_1-T/2+t_3-t_3+t_3=t_1+T/2-t_3$$

$$\Leftrightarrow TE-T=2(t_1-t_3)$$

$$\Leftrightarrow t_1=TE/2-T/2+t_3 \quad (12c)$$

It thus results that $$t_0=T-TE/2+T/2-t_3-T/2+t_3-t_3=T-TE/2-t_3 \quad (13a)$$

$$t_1=TE/2-T/2+t_3 \quad (13b)$$

$$t_2=T/2-t_3 \quad (13c)$$

This can be further simplified as $$t_1-t_2=TE/2-T/2+t_3-T/2+t_3=TE/2-T+2t_3$$

$$\Leftrightarrow t_3=\frac{1}{2}(T-TE/2+t_1-t_2) \quad (14)$$

These boundary conditions provided by the acquisition sequence are now combined with the conditions defined by the threshold for suppression of the unwanted coherence paths (Equations 11). This results as:

"+"  "−"

$$t_3 = 2(t_1 - t_2) = 1/2(T - TE/2 + t_1 - t_2) \quad t_3 = 2(t_2 - t_1) = 1/2(T - TE/2 + t_1 - t_2)$$

$$\Leftrightarrow 4(t_1 - t_2) = T - TE/2 + (t_1 - t_2) \quad 4(t_2 - t_1) = T - TE/2 - (t_2 - t_1)$$

$$\Leftrightarrow t_1 - t_2 = 1/3(T - TE/2) \quad t_2 - t_1 = 1/5(T - TE/2) \quad (15a)$$

$$t_1 - t_2 \geq M_{spoil}/G_D \quad t_2 - t_1 \geq M_{spoil}/G_D \quad (15b)$$

The gradient pulse durations with which the cited conditions are satisfied can now be calculated as follows:

$$t_0 = 1/6(2T-TE) \quad t_0 = 1/10(6T-3TE) \quad (16a)$$

$$t_1 = 1/6(T+TE) \quad t_1 = 1/10(-T+3TE) \quad (16b)$$

$$t_2 = 1/6(-T+2TE) \quad t_2 = 1/10(T+2TE) \quad (16c)$$

$$t_3 = 1/6(4T-2TE) \quad t_3 = 1/10(4T-2TE) \quad (16d)$$

The following additional condition is to be complied with:

$$t_1 - t_2 \geq M_{spoil}/G_D \quad t_2 - t_1 \geq M_{spoil}/G_D$$

$$\Leftrightarrow 1/3(T-TE/2) \geq M_{spoil}/G_D \quad 1/5(T-TE/2) \geq M_{spoil}/G_D \quad (17)$$

All times are positive, and TE>T applies, such that solutions exist for both cases when 2T−TE>0. Since T can then be calculated as $T=TE-t_{prep}-t_{adc}$, this condition can be written as $TE>2(t_{prep}+t_{adc})$ or $T>t_{prep}+t_{adc}$. For readout modules that require a great deal of time (for example high-resolution readout modules) and given low b-values, this condition limits the shortest achievable echo times. However, this is a basic limitation of the bipolar acquisition method that is not connected with the implicit suppression of unwanted coherence paths, as is apparent from FIG. 3 and Equations (2)-(4).

After the gradient moments are calculated by means of the gradient pulse durations, the acquisition of MR signals with the acquisition sequence ensues in Step (35). The diffusion coding gradients are activated with the determined gradient moments. An effective suppression of eddy currents results via the switching of these diffusion coding gradients, due to the bipolarity. The unwanted coherence paths are effectively suppressed via the switching with the gradient pulse durations determined in advance, with simultaneous rephasing of the double spin echo. As is also apparent from FIG. 3, the echo time TE is not thereby extended. In addition to the minimization of geometric distortions, a high signal-to-noise ratio can therefore be achieved. The reconstruction of image data can subsequently ensue from the magnetic resonance signals acquired with the readout module 52.

It should be clear that the methods illustrated in FIG. 2 can include additional steps that are conventionally used in a diffusion-weighted imaging. For example, an additional acquisition of MR signals with a similar acquisition sequence can ensue without switching of diffusion coding gradients in order to compare corresponding image data, for example by subtraction with the diffusion-weighted image data.

As is subsequently described with reference to FIG. 4, the acquisition sequence 50 shown in FIG. 3 can also be modified for the acquisition of diffusion-weighted MR signals with small b-values. As the acquisition sequence 50 in FIG. 3 shows, the acquisition sequence 70 shown in FIG. 4 can also be implemented with the magnetic resonance system shown in FIG. 1. As was already explained, the efficiency of the implicit suppression depends on the respective gradient amplitude of the diffusion coding gradients. Although an increase of the echo time TE generally relaxes the conditions, this is generally undesirable and furthermore is not possible for all values of $G_D$ (for example given a b-value of zero, and thus $G_D=0$). Therefore, additional spoiling or dephasing gradients are used in the embodiment shown in FIG. 4. According to the embodiment, given high diffusion gradient amplitudes the implicit suppression described with regard to FIG. 3 is used, and an additional, explicit suppression is used if the amplitude $G_D$ falls below a specific amplitude threshold. The strength of the explicit suppression can thereby be increased continuously with decreasing amplitude $G_D$. In the embodiment in FIG. 4, additional dephasing gradients 71 and 72 and 73 and 74 are activated immediately before and after the two refocusing pulses 54 and 55. By using a pair of identical gradient pulses, the double spin echo coherence path can remain unchanged. Such a grouping furthermore yields the smallest contribution of the additional gradients to the diffusion weighting, i.e. the smallest possible effect on the b-value. The gradient moments $M_A$ and $M_B$ of the first and second gradient pair are varied depending on the amplitude $G_D$ of the diffusion coding gradients. Furthermore, the dephasing gradients 71-74 are superimposed on the diffusion coding gradients 56-59. Significantly shorter TE times thus can be achieved, which increases the image quality due to a higher signal-to-noise ratio via reduction of the T2 relaxation. This is a significant advantage compared to conventional methods in which additional spoiler gradients have always led to an increase of the echo time.

By the use of these additional gradients, it is ensured that the amplitude of the superimposed dephasing and diffusion gradients remains within the limitations of the gradient system. Corresponding conditions for the acquisition sequence 70 can be derived by modification of Equations (5). In particular, the replacements of $M_0$ with $M_0+M_A$, $M_1$ with $M_1-M_A$, $M_2$ with $M_2+M_B$ and $M_3$ with $M_3-M_B$ are thereby implemented, which yields the following conditions:

1. FID $|M_0+M_A-M_1+M_A+M_2+M_B-M_3+M_B| \geq M_{spoil}$ (18a)

2. FID $|M_1+M_A+M_2+M_B-M_3+M_B| \geq M_{spoil}$ (18b)

3. FID $|-M_3+M_B| \geq M_{spoil}$ (18c)

1. SE $|M_0+M_A+M_1-M_A-M_2-M_B+M_3-M_B| \geq M_{spoil}$ (18d)

2. SE $|M_0+M_A-M_1+M_A+M_2+M_B+M_3-M_B| \geq M_{spoil}$ (18e)

3. SE $|M_1+M_A+M_2+M_B+M_3-M_B| \geq M_{spoil}$ (18f)

STE $|M_0+M_A+M_3-M_B| \geq M_{spoil}$ (18g)

ASTE $|M_0+M_A-M_3+M_B| \geq M_{spoil}$ (18h)

DSE $M_0+M_A+M_1-M_A-M_2-M_B-M_3+M_B=0$ (18i)

The algebraic signs of $M_A$ and $M_B$ can be both positive and negative. Use of the equation $M_0=-M_1+M_2+M_3$ (18i) yields 1. FID $2|-(M_1-M_2)+M_A+M_B| \geq M_{spoil}$ (19a)

2. FID $|-(M_1-M_2)-M_3+M_A+2M_B| \geq M_{spoil}$ (19b)

3. FID $|M_3-M_B| \geq M_{spoil}$ (19c)

1. SE $2|M_3-M_B|\geq M_{spoil}$ (19d)

2. SE $2|-(M_1-M_2)+M_3+M_A|\geq M_{spoil}$ (19e)

3. SE $|-(M_1-M_2)+M_3+M_A|\geq M_{spoil}$ (19f)

STE $|-(M_1-M_2)+2M_3+M_A-M_B|\geq M_{spoil}$ (19g)

ASTE $|-(M_1-M_2)+M_A+M_B|\geq M_{spoil}$ (19h)

$2|x|\geq|x|$ applies in turn, such that these can be simplified as $|-(M_1-M_2)-M_3+M_A+2M_B|\geq M_{spoil}$ (20a)

$|M_3-M_B|\geq M_{spoil}$ (20b)

$|-(M_1-M_2)+M_3+M_A|\geq M_{spoil}$ (20c)

$|-(M_1-M_2)+2M_3+M_A-M_B|\geq M_{spoil}$ (20d)

$|-(M_1-M_2)+M_A+M_B|\geq M_{spoil}$ (20e)

With the exception of the presence of $M_A$ and $M_B$, these inequalities are identical to the Inequalities (7). This means that these are already satisfied with $M_A=M_B=0$ for $M_3\geq|M_1-M_2|$ and $|M_1-M_2|\geq M_{spoil}$.

In the following the "+" case and the "−" case are differentiated again. Since the time progression of the acquisition sequence should not be varied depending on the b-values in order to avoid unwanted signal variations, the following selection is made (see Equation (11)):

"+"                          "−"

$M_3=2(M_1-M_2)$      $M_3=2(M_2-M_1)$ (21a)

It thus results that $|-3(M_1-M_2)+M_A+2M_B|\geq M_{spoil}|-(M_2-M_1)+M_A+2M_B|\geq M_{spoil}$ (22a)

$|2(M_1-M_2)-M_B|\geq M_{spoil}|2(M_2-M_1)-M_B|\geq M_{spoil}$ (22b)

$|(M_1-M_2)+M_A|\geq M_{spoil}|3(M_2-M_1)+M_A|\geq M_{spoil}$ (22c)

$|3(M_1-M_2)+M_A-M_B|\geq M_{spoil}|5(M_2-M_1)+M_A-M_B|\geq M_{spoil}$ (22d)

$|-(M_1-M_2)+M_A+M_B|\geq M_{spoil}|(M_2-M_1)+M_A+M_B|\geq M_{spoil}$ (22e)

An explicit suppression can be used in the present embodiment if $M_1-M_2<M_{spoil} M_2-M_1<M_{spoil}$ (23)

(see Equation (11)).

Under consideration of these equations and under consideration of solutions with continuously increasing gradient moments of the dephasing gradients (which are zero if condition (23) occurs), the following solutions for $M_A$ and $M_B$ can be selected:

$M_A=M_{spoil}-(M_1-M_2) M_A=3M_{spoil}-3(M_2-M_1)$ (24a)

$M_B=-2M_A M_B=-2M_A$ (24b)

Furthermore, a condition for this is set in the following: that the superimposition of the dephasing gradients with the diffusion coding gradients remains below the limits provided by the hardware. For a given dephasing moment, the amplitude of the necessary dephasing gradients depends on the available time. With reference to FIG. 4, the time $t_{min}^A$ that is available for switching the dephasing moment $M_A$ is equal to the minimum of the time spans $t_0$ and $t_1$. The time $t_{min}^B$ that is available for switching the dephasing moment $M_B$ is accordingly equal to the minimum of the time spans $t_2$ and $t_3$. The magnitude of the amplitude $G_{spoil}$ of the dephasing gradients is calculated as $G_{spoil}^A=(M_{spoil}-G_D(t_1-t_2))/t_{min}^A G_{spoil}^A=3(M_{spoil}-G_D(t_2-t_1))/t_{min}^A$ (25a)

$G_{spoil}^B=2(M_{spoil}-G_D(t_1-t_2))/t_{min}^B G_{spoil}^B=6(M_{spoil}-G_D(t_2-t_1))/t_{min}^B$ (25b)

wherein the amplitude falls in the range $G_D\in[0,M_{spoil}/(t_1-t_2)] G_D\in[0,M_{spoil}/(t_2-t_1)]$ (26)

add the amplitude $G_{spoil}$ falls in the ranges $G_{spoil}^A\in[0,M_{spoil}/t_{min}^A] G_{spoil}^A\in[0,3M_{spoil}/t_{min}^A]$ (27a)

$G_{spoil}^B\in[0,2M_{spoil}/t_{min}^B] G_{spoil}^B\in[0,6M_{spoil}/t_{min}^B]$ (27b)

The sum of the dephasing gradients and diffusion gradients should remains below the maximum amplitude $G_{max}$ limited by the gradient system that is used:

$G_{spoil}^A+G_D\leq G_{max} G_{spoil}^A+G_D\leq G_{max}$ (28a)

$\Leftrightarrow G_D(1(t_1-t_2)/t_{min}^A)+M_{spoil}/t_{min}^A\leq G_{max} G_D(1-3(t_2-t_1)/t_{min}^A)+3M_{spoil}/t_{min}^A\leq G_{max}$ $G_{spoil}^B+G_D\leq G_{max} G_{spoil}^B+G_D\leq G_{max}$ (28b)

$\Leftrightarrow G_D(1-2(t_1-t_2)/t_{min}^B)+2M_{spoil}/t_{min}^B\leq G_{max} G_D(1-6(t_2-t_1)/t_{min}^B)+6M_{spoil}/t_{min}^B\leq G_{max}$ Since the left side of these inequalities increases linearly with $G_D$, it is sufficient to evaluate the extreme values in order to check whether the Inequalities (28) are satisfied:

Min: $M_{spoil}/t_{min}^A\leq G_{max} 3M_{spoil}/t_{min}^A\leq G_{max}$

Max: $M_{spoil}/(t_1-t_2)\leq G_{max} M_{spoil}/(t_2-t_1)\leq G_{max}$ (29a)

Min: $2M_{spoil}/t_{min}^B\leq G_{max} 6M_{spoil}/t_{min}^B\leq G_{max}$

Max: $M_{spoil}/(t_1-t_2)\leq G_{max} M_{spoil}/(t_2-t_1)\leq G_{max}$ (29a)

If these conditions are satisfied, it is thus possible to superimpose the required dephasing gradients on the diffusion coding gradients without exceeding the limitations provided by the gradient system. It can thus be established that the "+" case is less limiting than the "−" case.

Via use of the additional dephasing gradients 71-74, unwanted coherence paths in the acquisition sequence 70 (shown in FIG. 4) can thus also be effectively suppressed for low b-values, i.e. for small amplitudes of the diffusion coding gradients. In particular, this is achieved without extending the echo time TE.

Furthermore, it is possible to introduce an additional degree of freedom in that pauses are incorporated into the diffusion module 51. Although this can reduce the efficiency of the diffusion coding, it is possible if necessary to extend the range of available solutions.

According to a first alternative, an additional pause $t_P$ is introduced between the gradients 57 and 58, i.e. between $t_1$ and $t_2$. Equations (2)-(4) can be adapted with this additional pause $t_P$. Since the additional pause does not affect the development of the magnetization, the calculations described in the preceding can be used with corresponding adaptations. The following time spans for the gradients of the diffusion module thereby result in turn for the "+" case and "−" case:

"+"                                                  "−"

$t_3 = 2(t_1 - t_2) = 2/3T - 1/3TE$          $t_3 = 2(t_2 - t_1) = 2/5T - 1/5TE$                                    (37)
$t_2 = T/2 - t_p/2 - t_3 = -1/6T + 1/3TE - t_p/2$     $t_2 = T/2 - t_p/2 - t_3 = 1/10T + 1/5TE - t_p/2$
$t_1 = TE/2 - T/2 - t_p/2 + t_3 = 1/6T + 1/6TE - t_p/2$  $t_1 = TE/2 - T/2 - t_p/2 + t_3 = -1/10T + 3/10TE$
$t_p/2$
$t_0 = T - TE/2 - t_3 = 1/3T - 1/6TE$        $t_0 = T - TE/2 - t_3 = 3/5T - 3/10TE$

From this it is clear that $t_0$ and $t_3$ remain unchanged while $t_1$ and $t_2$ are reduced by $t_p/2$. The condition 2T−TE>0 is not altered.

In a further alternative, a pause $t_p/2$ is inserted after $t_0$ and before $t_3$. Equations (2)-(4) can in turn be adapted accordingly. For this case the way of calculating the gradient pulse durations $t_i$ that is indicated above can also be analogously applied. The time spans result as:

"+"                                                  "−"

$t_0 = 1/6(2T - TE - 2t_p)$        $t_0 = 1/10(6T - 4TE - 6t_p)$      (47)
$t_1 = 1/6(T + TE - t_p)$          $t_1 = 1/10(-T + 3TE + t_p)$
$t_2 = 1/6(-T + 2TE + t_p)$        $t_2 = 1/10(T + 2TE - t_p)$
$t_3 = 1/6(4T - 2TE - 4t_p)$       $t_3 = 1/10(4T - 2TE - 4t_p)$

As is apparent from the equations, the condition is exacerbated for $t_0$. The condition 2T−TE>0 is not forgone. This condition should be satisfied in both alternatives in order to ensure an optimally comprehensive suppression of the unwanted signal coherence paths. As already mentioned, this is a general limitation of bipolar diffusion coding sequences.

According to a further embodiment it is provided to use an additional refocusing pulse in order to loosen this condition. However, the generation of additional coherence paths and the additional required time for the radiation of the RF pulse can thereby be disadvantageous.

Furthermore, it is possible to maximize the time span T in order to additionally improve the conditions for the use of the time progression according to the embodiments described in the preceding. For example, this can be achieved by use of shorter preparation times $t_{prep}$ and shorter readout times $t_{adc}$. This can be realized by short echo trains (for example low resolution, small echo interval, partial k-space scanning, iPAT or the like).

For an additional improvement it is possible to shift the point at which the spin echo condition (3) is satisfied to earlier points in time (i.e. the spin echo does not coincide with the acquisition of the k-space center). The time $t_{adc}$ is therefore effectively reduced. This can lead to a small contribution of $T_2^*$ relaxation in the center of k-space instead of a pure $T_2$ relaxation. However, the echo time $t_2$ can be reduced by up to a factor of $2\Delta t_{adc}$ depending on the sequence that is used.

In the following, results are provided that were achieved with an embodiment of the method according to the invention and the magnetic resonance system according to the invention. Table 1 shows examples of the smallest achieved echo times TE for different b-values and for three different acquisition sequences (monopolar Stejskal-Tanner sequence, a conventional bipolar sequence with additional, separate spoiler gradients, and an embodiment of the "bipolar +" acquisition sequence according to the invention). Two imaging protocols with different resolutions were used. The following values were used for the standard resolution:

Field of view FOV=230×230 mm; resolution RES=128× 128; slice thickness SL=5 mm; partial Fourier acquisition PF=6/8; bandwidth BW=1502 Hz/pixel; echo interval ES=0.73 ms. The following minimum echo times were achieved for the three acquisition sequences:

| b-value [s/mm$^2$] | monopolar | bipolar | bipolar+ |
|---|---|---|---|
| 0 | 63 ms | 86 ms | 81 ms |
| 500 | 72 ms | 86 ms | 81 ms |
| 1000 | 79 ms | 89 ms | 81 ms |
| 2000 | 87 ms | 99 ms | 91 ms |
| 5000 | 114 ms | 120 ms | 113 ms |
| 10000 | 143 ms | 147 ms | 135 ms |

The following values were used for the imaging protocol with increased resolution: FOV=230×230 mm; RES=192× 192; iPAT2, SL=5 mm; PF=6/8; BW=1184 Hz/pixel; ES=0.94 ms. The following minimum echo times therefore result:

| B-value [s/mm$^2$] | monopolar | bipolar | bipolar+ |
|---|---|---|---|
| 0 | 62 ms | 87 ms | 82 ms |
| 500 | 70 ms | 87 ms | 82 ms |
| 1000 | 77 ms | 94 ms | 82 ms |
| 2000 | 85 ms | 106 ms | 95 ms |
| 5000 | 115 ms | 127 ms | 117 ms |
| 10000 | 143 ms | 149 ms | 139 ms |

It is clear that the bipolar+ sequence according to an embodiment of the invention achieves shorter echo times for the entire considered region of b-values than the conventional bipolar method. Compared with the monopolar method, the bipolar+ method requires slightly longer echo times for b-values of 1000 s/mm$^2$ (≦5 ms difference) and achieves even shorter echo times for b-values over 5000 s/mm$^2$.

Figure 5:
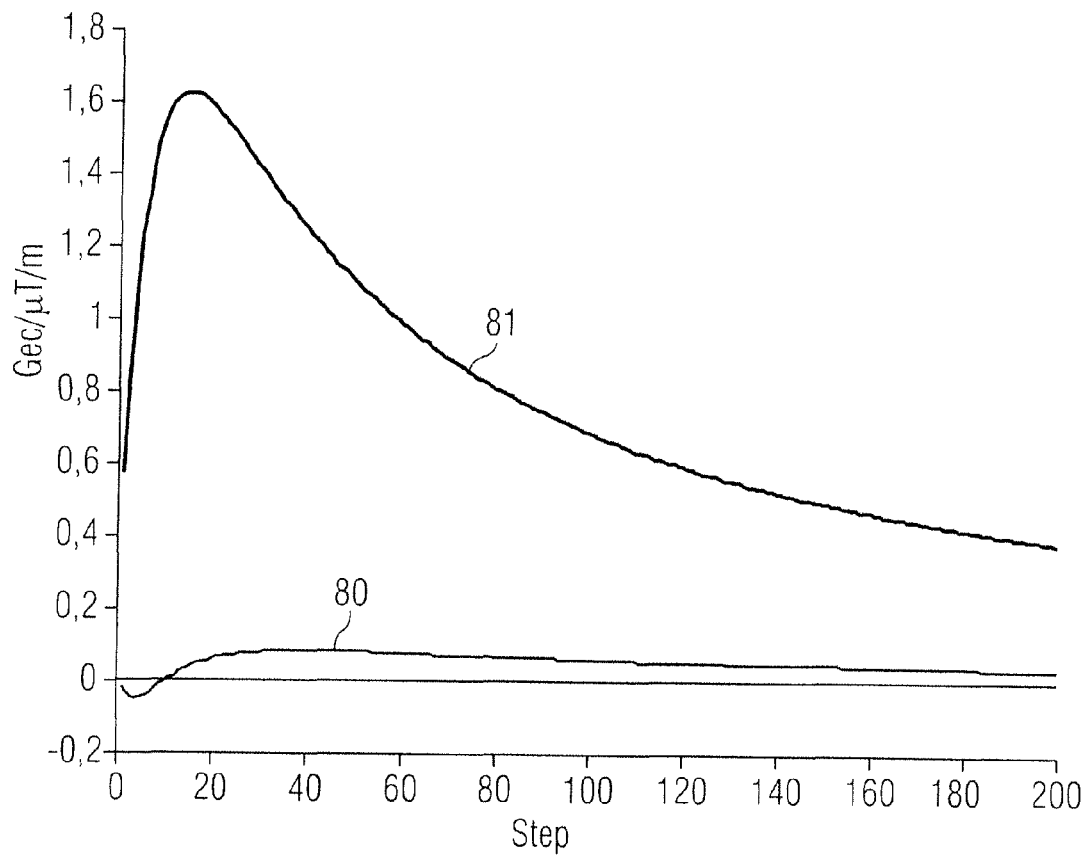
FIG. 5 shows the amplitude of eddy currents remaining in the k-space center, depending on the eddy current time constant.

However, eddy currents can be suppressed significantly more efficiently with the method according to the invention than with the monopolar method. This is illustrated in FIG. 5. The remaining dynamic field distortions were estimated using rectangular diffusion gradient profiles which cause exponentially decaying eddy currents with a single time constant. FIG. 3 shows the dependency of the remaining eddy current amplitude in the k-space center on the time constants of the eddy currents. Curve 81 shows the amplitude for a monopolar method in which a constant gradient is switched during the time period T and curve 80 shows the estimation of the amplitude given use of the bipolar+ method. For both cases a diffusion coding with a maximum gradient amplitude and a pre-equalization was assumed; the eddy current fields were reduced to 0.01% of the original amplitude. A remaining exposure field of 1 μT/m corresponds to a maximum registration error of half of a pixel within a field of view of 230 mm. Although the time progression of the bipolar+ method was not optimized for a maximum compensation of the eddy currents, the use of the bipolar gradient pulses reduces the remaining eddy current fields by a factor of 5-10 compared with the monopolar method. This shows that the bipolar+ method also effectively suppresses eddy currents and avoids corresponding image disruptions while short TE times are simultaneously achieved.

In order to appropriately examine the unwanted coherence paths, multiple diffusion-weighted images with multiple diffusion directions were acquired. For example, image data for 6, 10, 12, 20, 32 and 46 directions as well as image data with b-values of 0.50 s/mm$^2$, 500 s/mm$^2$ and 1000 s/mm$^2$ were acquired. Furthermore, image data with b-values of 0 and 1000 s/mm$^2$ were acquired for 256 directions, both with normal diffusion vector orientations and inverted diffusion vector orientations. No indications for signal portions of unwanted coherence paths could be learned from the image data acquired with the bipolar+ method. In particular, no interferences ("banding artifacts") were visible.

Figure 6:
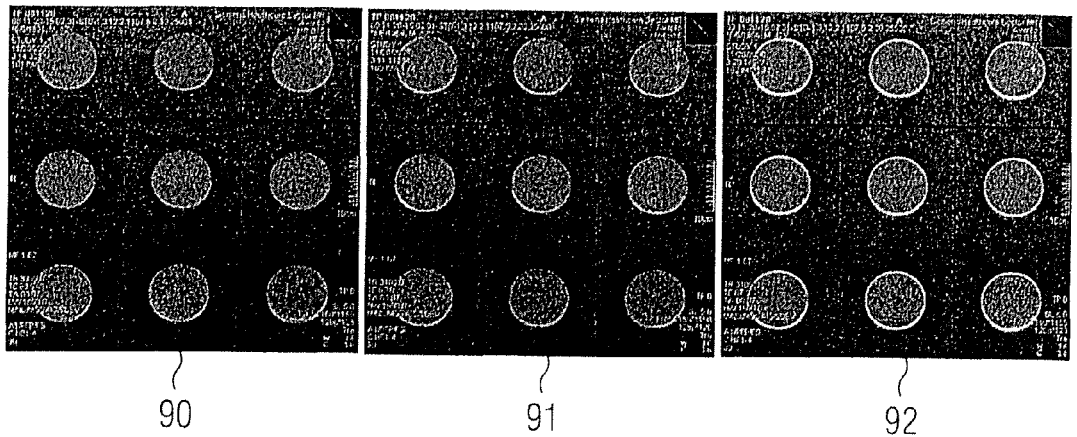
FIG. 6 illustrates a comparison of magnetic resonance data acquired with conventional methods with magnetic resonance data that were acquired with an embodiment of the method according to the invention.

Image data for 20 diffusion directions were acquired with a conventional bipolar method (90), with the new bipolar+ method (91) and with a standard monopolar method (92). FIG. 6 shows a standard deviation chart for each of the three methods. These illustrate spatial distortions due to orientation-dependent eddy currents (light contours). With the bipolar+ method (91), the eddy current-induced distortions are only slightly greater than with a conventional bipolar method (90). However, they are significantly smaller in comparison with the monopolar methods (92). It is noted that the conventional method is hereby optimized for the reduction of these eddy currents. At the same time, the bipolar+ method enables a reduction of the echo time by approximately 10% (8 ms in this example) in comparison to the conventional bipolar method for the acquisition sequence used here.

The features of the embodiments described in the preceding can be combined. The embodiments described in the preceding have a double spin echo acquisition sequence with four diffusion coding gradients and an EPI or segmented EPI readout module. In other embodiments of the method according to the invention and the magnetic resonance system according to the invention, other acquisition sequences can also be used, for example with additional or with fewer diffusion coding gradients, additional RF pulses and other readout modules.

Unwanted coherence paths can be effectively suppressed via the optimization of the gradient moments of the diffusion coding gradients depending on the readout module. The method combines the advantages of conventional bipolar methods (low eddy current-induced disruptions, uniform distribution of the gradient load on both GPA polarities) with those of conventional monopolar methods (short echo times). Moreover, the activation of additional spoiler gradients that do not extend the echo time (as described above) is advantageous for imaging. Measurements of phantoms have shown applicability and the efficiency of the method. For example, the invention can be used to improve the image quality for an in vivo diffusion imaging.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for diffusion-weighted acquisition of magnetic resonance (MR) signals, comprising the steps of:
   acquiring MR signals from an examination subject located in an MR data acquisition unit by operating the MR data acquisition unit to implement an MR signal acquisition sequence configured to acquire MR signals that correspond to a predetermined signal coherence path, said MR signal acquisition sequence comprising a diffusion module comprising multiple diffusion coding gradients that are activated with respective, predetermined gradient moments, and a readout module comprised of readout gradients; and
   setting the respective gradient moments of said diffusion coding gradients with a threshold that causes MR signals in coherence paths other than said predetermined coherence path to be reduced compared to the MR signals corresponding to said predetermined signal coherence path.

2. A method as claimed in claim 1 comprising selecting said threshold dependent on said readout module.

3. A method as claimed in claim 2 wherein said readout gradients of said readout module exhibit a readout gradient moment, and setting said threshold dependent on said readout gradient moment.

4. A method as claimed in claim 1 comprising setting said threshold to define a minimum dephasing gradient moment that, by setting said gradient moments of the diffusion coding gradients with respect to said threshold, causes diffusion coding gradients that occur in each of said other coherence paths to have respective gradient moments that are at least as large as said minimum dephasing gradient moment.

5. A method as claimed in claim 1 comprising entering the MR signals acquired from the examination subject into k-space in a k-space memory, and setting said threshold to cause central positions in k-space of MR signals in said other coherence paths to be outside of k-space in said k-space memory in which said MR signals acquired from the examination subject are entered.

6. A method as claimed in claim 1 wherein said threshold defines a minimal dephasing gradient moment $M_{spoil}$, and determining said threshold according to the equation $$M_{spoil} = N \cdot M_{readout}$$

wherein $N \geq 1$, and wherein $M_{readout} = RES/(\gamma \cdot FOV)$, wherein RES designates a resolution of the readout module, FOV designates a field of view of the readout module, and $\gamma$ designates the gyromagnetic ratio.

7. A method as claimed in claim 1 wherein said diffusion module comprises four diffusion coding gradients each having a link that, in part, defines the gradient moment thereof, and comprising setting said gradient moments of the respective diffusion coding gradients by adjusting the respective links thereof as setting parameters, with three of said setting parameters being determined by three conditions established by said acquisition sequence, and a fourth of said parameters is determined dependent on said threshold.

8. A method as claimed in claim 7 comprising determining said fourth of said parameters by comparing, to said threshold, gradient moments of respective diffusion coding gradients in said other coherence paths.

9. A method as claimed in claim 1 wherein each of said diffusion coding gradients in said diffusion module has a length that, in part, defines the gradient moment thereof, and comprising setting the respective gradient moments of the diffusion coding gradients in said diffusion module by adjusting the respective lengths thereof dependent on a total duration of activation of said diffusion coding gradients in said MR signal acquisition sequence, a rephasing of magnetization in the predetermined coherence paths produced by said diffusion coding gradients in said diffusion module, and an adaptation of respective pulse durations of said diffusion coding gradients to cause a rephasing of a spin echo generated by said MR signal acquisition sequence to occur at a predetermined MR signal acquisition point in time of said readout module.

10. A method as claimed in claim 1 wherein said diffusion module comprises at least four diffusion gradients, and, in said MR signal acquisition sequence, activating two of said at least four diffusion gradients respectively in opposite directions.

11. A method as claimed in claim 1 comprising selecting said readout module from the group consisting of an echoplanar imaging readout sequence and a segmented echo planar imaging readout sequence.

12. A method as claimed in claim 1 wherein said diffusion module additionally comprises multiple dephasing gradients that produce an additional reduction of the MR signals in said other coherence paths.

13. A method as claimed in claim 12 wherein each of said multiple dephasing gradients has a dephasing gradient moment and a polarity, and comprising setting at least one of the respective dephasing gradient moments and polarity of the multiple dephasing gradients dependent on said threshold.

14. A method as claimed in claim 12 comprising superimposing said dephasing gradients on said diffusion coding gradients in said diffusion module.

15. A method as claimed in claim 12 comprising activating said dephasing gradients in said diffusion module when an amplitude of the respective diffusion coding gradients falls below a predetermined amplitude threshold.

16. A method as claimed in claim 12 wherein each of said diffusion coding gradients has an amplitude, and each of said dephasing gradients has a gradient moment, and comprising adjusting the respective gradient moments of the dephasing gradients in said diffusion module depending on the amplitude of the diffusion coding gradients in the diffusion module.

17. A method as claimed in claim 12 wherein each of said dephasing gradients has a dephasing gradient moment and wherein said threshold also defines a minimum dephasing gradient moment, and comprising setting the gradient moments of the diffusion coding gradients and the dephasing gradient moments to cause a gradient moment in each of said other coherence paths that results from said diffusion coding gradients and said dephasing gradients in said diffusion module, to be at least as large as said minimum dephasing gradient moment.

18. A method as claimed in claim 1 wherein said diffusion module comprises a pause, having a pause duration, between two successive diffusion coding gradients in said diffusion module, and comprising varying said pause duration to produce an additional degree of freedom for setting the gradient moments of the diffusion coding gradients.

19. A method as claimed in claim 1 comprising employing, as said MR signal acquisition sequence, a double spin echo sequence comprising two refocusing pulses.

20. A method as claimed in claim 19 comprising selecting said other coherence paths, in which said MR signals are reduced by setting said gradient moments of said diffusion coding gradients in said diffusion module, from the group consisting of three induction decays that arise from said double spin echo sequence, three spin echoes that arise from said double spin echo sequence, and two stimulated echoes that arise from said double spin echo sequence.

21. A magnetic resonance system for diffusion-weighted acquisition of magnetic resonance (MR) signals, comprising:
an MR data acquisition unit;
a control unit configured to operate said MR data acquisition unit to acquire MR signals from an examination subject located in said MR data acquisition unit by implementing an MR signal acquisition sequence configured to acquire MR signals that correspond to a predetermined signal coherence path, said MR signal acquisition sequence comprising a diffusion module comprising multiple diffusion coding gradients that are activated with respective, predetermined gradient moments, and a readout module comprised of readout gradients; and
said control unit being configured to set the respective gradient moments of said diffusion coding gradients with a threshold that causes MR signals in coherence paths other than said predetermined coherence path to be reduced compared to the MR signals corresponding to said predetermined signal coherence path.

22. A non-transitory computer-readable storage medium encoded with programming instructions, said storage medium being loaded into a computerized control and data processing system of a magnetic resonance (MR) system, and said programming instructions causing said computerized control and data processing system to:
acquire MR signals from an examination subject located in an MR data acquisition unit of the MR system by operating the MR data acquisition unit to implement an MR signal acquisition sequence configured to acquire MR signals that correspond to a predetermined signal coherence path, said MR signal acquisition sequence comprising a diffusion module comprising multiple diffusion coding gradients that are activated with respective, predetermined gradient moments, and a readout module comprised of readout gradients; and
set the respective gradient moments of said diffusion coding gradients with a threshold that causes MR signals in coherence paths other than said predetermined coherence path to be reduced compared to the MR signals corresponding to said predetermined signal coherence path.

* * * * *